United States Patent [19]
Comins et al.

[11] Patent Number: 5,264,579
[45] Date of Patent: Nov. 23, 1993

[54] D RING INTERMEDIATES FOR THE SYNTHESIS OF CAMPTOTHECIN AND CAMPTOTHECIN ANALOGS

[75] Inventors: Daniel L. Comins; Matthew F. Baevsky, both of Cary

[73] Assignee: North Carolina State University, N.C.

[21] Appl. No.: 36,053

[22] Filed: Mar. 23, 1993

Related U.S. Application Data

[60] Division of Ser. No. 900,650, Jun. 18, 1992, Pat. No. 5,212,317, which is a continuation-in-part of Ser. No. 632,970, Dec. 20, 1990, Pat. No. 5,162,532.

[51] Int. Cl.$^5$ .............................................. C07D 213/64
[52] U.S. Cl. ...................................... 546/301; 546/302
[58] Field of Search ................................. 546/301, 302

[56] References Cited

U.S. PATENT DOCUMENTS 3,109,018 10/1963 Hanover .............................. 260/475
3,607,651 9/1971 Moroz ................................. 195/30

(List continued on next page.)

FOREIGN PATENT DOCUMENTS 0325247 4/1989 European Pat. Off.

(List continued on next page.)

OTHER PUBLICATIONS

R. Lawrence, "The Resolution and Use of Chiral Auxiliaries in Asymmetric Synthesis," Dissertation presented (List continued on next page.)

*Primary Examiner*—Bernard Dentz
*Attorney, Agent, or Firm*—Bell Seltzer Park & Gibson

[57] ABSTRACT

Processes for making compounds of Formulae XIV, XV, and XVII

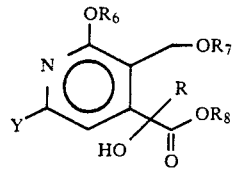

XIV

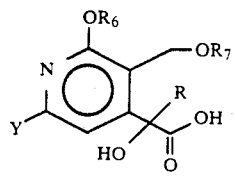

XV

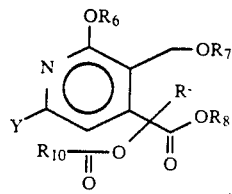

XVII wherein $R_6$ is lower alkyl, $R_7$ is lower alkyl, R is lower alkyl, Y is H, F or Cl, $R_8$ is a compound of Formula

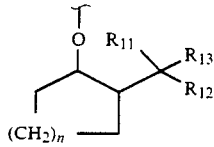

(XVIII)

wherein n is 1, 2, or 3, $R_{11}$ is $C_1$-$C_4$ alkyl and $R_{12}$ is the same as $R_{11}$, or $R_{11}$ and $R_{12}$ together form cyclopentane or cyclohexane, and $R_{13}$ is:

(a) phenyl substituted 1 to 5 times with $C_3$-$C_7$ secondary alkyl or $C_4$-$C_7$ tertiary alkyl, or
(b) selected from the group consisting of naphthyl, anthryl, and phenanthryl optionally substituted 1 to 5 times with $C_3$-$C_7$ secondary alkyl or $C_4$-$C_7$ tertiary alkyl groups, $R_{10}$ is $C_6$-$C_{10}$ alkyl, aryl or alkyl aryl, and Y is H, F or Cl, are disclosed. These processes can be used to make optically enhanced and optically pure forms of the compounds, which are useful in the making of camptothecin and analogs thereof.

15 Claims, No Drawings

U.S. PATENT DOCUMENTS

| | | |
|---|---|---|
| 3,943,181 | 3/1976 | Fleischer et al. ............... 260/631 R |
| 4,418,225 | 11/1983 | House ................................ 568/829 |
| 4,578,381 | 3/1986 | Uchida et al. ...................... 514/233 |
| 4,720,558 | 1/1988 | Kaulen ............................... 549/443 |
| 4,894,456 | 1/1990 | Wall et al. ............................ 546/41 |
| 4,916,074 | 4/1990 | Yoshida et al. ..................... 435/280 |
| 4,962,031 | 10/1990 | Yoshida et al. ..................... 435/280 |
| 4,963,492 | 10/1990 | Keller et al. ........................ 435/280 |
| 4,996,158 | 2/1991 | Oda et al. ........................... 435/280 |
| 5,021,345 | 6/1991 | Urban et al. ........................ 435/180 |
| 5,032,523 | 7/1991 | Amano et al. ...................... 435/280 |
| 5,057,427 | 10/1991 | Wald et al. .......................... 435/280 |

(List continued on next page.)

FOREIGN PATENT DOCUMENTS

| | | |
|---|---|---|
| 52-51095 | 1/1977 | Japan . |
| 54-101487 | 7/1979 | Japan . |
| 1-235599 | 6/1989 | Japan . |

(List continued on next page.)

OTHER PUBLICATIONS to the faculty of the University of Texas at Austin (UMI) Ann Arbor, Mich.) Dec., 1988.
R. Benkeser et al., *J. Am. Chem. Soc.* 85, 3984–3989 (1963).
G. Langrand et al., *Tetrahedron Letters* 26, No. 15, 1857–1860 (1985).
W. Oppolzer et al., *Helvetica Chimica Acta* 63, Fasc. 7, 2015–2018 (1980).
J. Whitesell, *Acc. Chem. Res.* 18, 280–284 (1985).
J. Whitesell and R. Lawrence, *Chimia* 40, No. 9, 318–322 (1986).
D. Wilhelm et al., *J. Am. Chem. Soc.* 106, No. 2, 361–367 (1984).
Lyle et al., 23d *International Congress of Pure and Applied Chemistry* (Boston, Mass. 1971), p. 67.
Portlock et al., *Org. Chem.* 38, No. 13, 2351–2355 (1973).
Plattner et al., *J. Amer. Chem. Soc.* 94, No. 24, 8613–8615 (1972).
Sugasawa et al., *Chem. Pharm. Bull.* 22, No. 4, 763–770 (1974).
"Heterocyclic Compounds: Pyridine and Its Derivatives", vol. 14, Supplement Part 3 (John Wiley & Sons, Inc., Ed. Abramovitch), pp. 745–753 (1974).
Bristol et al., *Journal of Medicinal Chemistry* 18, No. 5, 535 (1975).
Cai et al., *The Alkaloids* XXI, 101 (Academic Press 1983).
Comins et al., *J. Org. Chem.* 55, No. 1, 69 (1990).
Comins et al., *J. Org. Chem.* 54, No. 15, 3730 (1989).
Comins et al., *Tetrahedron Letters* 29, No. 7, 773 (1988).
Comins et al., *J. Org. Chem.* 49, No. 6, 1078 (1984).
Comins, PhD Thesis, University of New Hampshire, Durham, N.H., pp. 25–29 (1977).
Doyle et al., *J. Am. Chem. Soc.* 94, No. 10, 3659 (1972).
R. Grigg et al., *Tetrahedron* 46, No. 11, 4003 (1990).
Larock, "Comprehensive Organic Transformations: A Guide to Functional Group Preparations," (VCH Publishers, Inc., New York, N.Y.) pp. 467–468 (1989).
Larock, "Comprehensive Organic Transformations: A Guide to Functional Group Preparations," (VCH Publishers, Inc., New York, N.Y.) pp. 501–504 (1989).
Lyle et al., *J. Org. Chem.* 38, No. 19, 3268 (1973).
Lyle et al., *J. Org. Chem.* 37, No. 24, 3967 (1972).
March, "Advanced Organic Chemistry: Reactions, Mechanisms, and Structure," Third Edition, (John Wiley & Sons, Inc.) pp. 510–511 (1985).
"Natural Products Chemistry," vol. 2 (Academic Press, Inc., Ed. K. Nakanishi et al.), pp. 358–361 (1981).
"Natural Products Chemistry," vol. 3 (Academic Press, Inc., Ed. K. Nakanishi et al.), pp. 573–574 (1982).
Schmidt, *Aldrichimica Acta,* 14, No. 2, 31 (1981).

D RING INTERMEDIATES FOR THE SYNTHESIS OF CAMPTOTHECIN AND CAMPTOTHECIN ANALOGS

Related Applications

This application is a divisional of prior application Ser. No. 07/900,650, filed Jun. 18, 1992, now U.S. Pat. No. 5,212,317, the disclosure of which is incorporated by reference herein in its entirety which application is a continuation-in-part of U.S. patent application Ser. No. 07/632,970, filed 20 Dec. 1990 now U.S. Pat. No. 5,162,532, the disclosure of which is incorporated herein by reference in its entirety.

FIELD OF THE INVENTION

The present invention provides a parallel synthesis of camptothecin and camptothecin analogs via novel intermediates at high yields.

BACKGROUND OF THE INVENTION

Camptothecin (Chem. Abstracts Registry No. 7689-03-4) is a naturally occurring compound found in *Camptotheca acuminata* (Nyssaceae) which has antileukemic and antitumor properties. Numerous camptothecin analogs having like properties are known, examples being those described in U.S. Pat. No. 4,894,456 to Wall et al. and European Patent Application No. 0 325 247 of Yaegashi et al.

A number of syntheses for camptothecin are known. Several routes are reviewed in *Natural Products Chemistry*, Vol. 2, 358-361 (K. Nakanishi, T. Goto, S. Ito, S. Natori and S. Nozoe eds.) and in J. Cai and C. Hutchinson, Camptothecin, in *The Alkaloids*, Vol. XXI, 101-137 (Academic Press 1983). The biosynthesis of camptothecin is described in *Natural Products Chemistry*, Vol. 3, 573-574 (K. Nakanishi et al. eds.). A recent synthetic route is described in U.S. Pat. No. 4,894,456 to Wall et al. (see also references cited therein).

A problem with prior methods of synthesizing camptothecin is that they are largely linear syntheses. Such syntheses provide low yields of the final product because of the sequential loss in product during each step of the total synthesis. Parallel syntheses (i.e., a strategy in which two synthetic paths are followed separately and the products thereof combined to form the final product) provide higher yields, but few such syntheses have been available for camptothecin. Accordingly, an object of the present invention is to provide a parallel synthetic method for making camptothecin and analogs thereof.

SUMMARY OF THE INVENTION

The present invention provides a process for making compounds of Formulae XIV, XV, and XVII below:

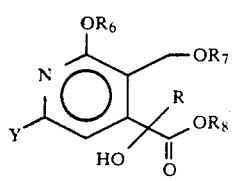

XIV

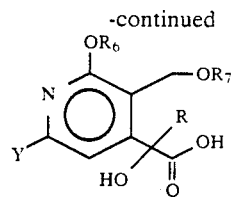

XV

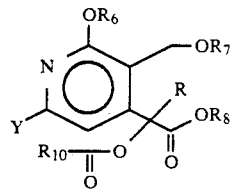

XVII wherein $R_6$ is lower alkyl, $R_7$ is lower alkyl, R is lower alkyl, Y is H, F or Cl, $R_8$ is a compound of Formula XVIII

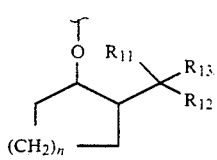

(XVIII)

wherein n is 1, 2, or 3, $R_{11}$ is $C_1$–$C_4$ alkyl and $R_{12}$ is the same as $R_{11}$, or $R_{11}$ and $R_{12}$ together form cyclopentane or cyclohexane, and $R_{13}$ is:

(a) phenyl substituted 1 to 5 times with $C_3$–$C_7$ secondary alkyl or $C_4$–$C_7$ tertiary alkyl, or (b) selected from the group consisting of naphthyl, anthryl, and phenanthryl optionally substituted 1 to 5 times with $C_3$–$C_7$ secondary alkyl or $C_4$–$C_7$ tertiary alkyl groups, $R_{10}$ is $C_6$–$C_{10}$ alkyl, aryl or alkyl aryl, and Y is H, F or Cl. These compounds are useful in the production of compouncs or Formula III,

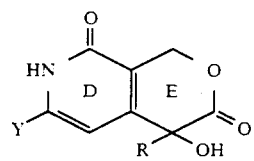

(III)

wherein R and Y are as defined above, which in turn is useful in the production of compounds of Formula I.

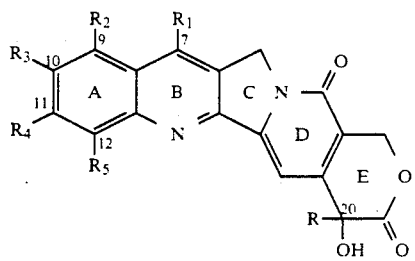

(I)

wherein:
R may be loweralkyl,
$R_1$ may be H, loweralkyl, loweralkoxy, or halo,
$R_2$, $R_3$, $R_4$, and $R_5$ may each independently be H, amino, hydroxy, loweralkyl, loweralkoxy, loweralkylthio, di(loweralkyl)amino, cyano, methylenedioxy, Formyl, nitro, halo, trifluoromethyl, amninomethyl, azido, amido, hydrazino, or any of the twenty standard amino acids bonded to the A ring via the amino-nitrogen atom (numbering in Formula I is by the Le Men-Taylor numbering system and rings are lettered in the conventional manner. See J. Cai and C. Hutchinson, supra at 102).

In one embodiment illustrated by Scheme D, propoxy, sec-butoxy, and isohexoxy; examples of loweralkylthio groups are methylthio, ethylthio, tert-butylthio, and hexylthio; and examples of di(loweralkyl)amino groups are dimethylamino, diethylamino, diisopropylamino, di(n-butyl)amino, and dipentylamino.

The terms "halo" and "halogen" as used herein refers to a substituent which may be fluoro, chloro, bromo, or iodo.

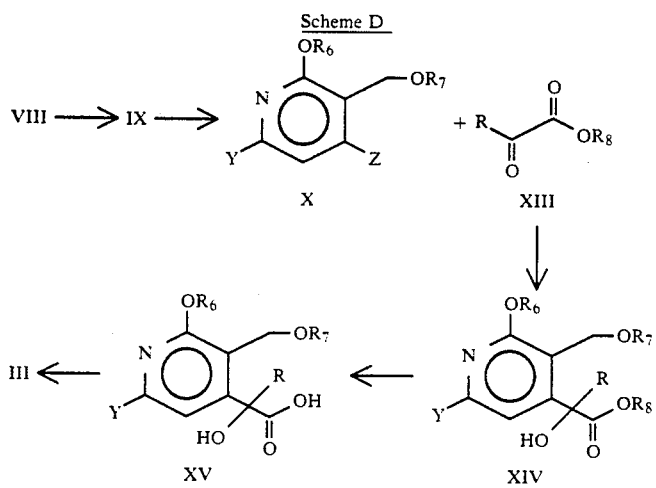

$R_8$ is optically pure, which can lead to a diastereomerically enhanced compound XIV and optically enhanced compounds XV, III, and I. In another embodiment illustrated by Scheme E, Substituents on the "A" ring of the compounds disclosed herein may be joined together to form a bifunctional substituent such as the methylenedioxy group. Methylenedioxy substituents may be bonded to any two

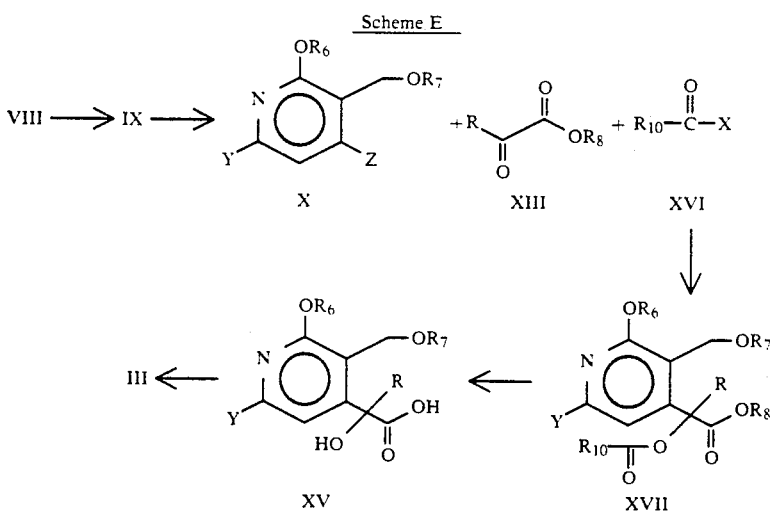

the use of optically pure $R_8$ can lead to a diastereomerically pure compound XVII, which in turn can be used to produce diastereometrically pure forms of compound XV and optically pure forms of compounds III and I.

DETAILED DESCRIPTION OF THE INVENTION

As used herein, the term "loweralkyl" means a linear or branched alkyl group with 1-8, preferably 1-4, carbon atoms, such as methyl, ethyl, propyl, isopropyl, n-butyl, tert-butyl, hexyl, and octyl. This definition also applies to a loweralkyl moiety in the loweralkoxy, loweralkylthio, and di(loweralkyl)amino groups. Thus, examples of loweralkoxy groups are methoxy, ethoxy, consecutive positions in the A ring, for example, the 9,10, the 10,11, or the 11,12 positions.

Substituents which are standard amino acids may be any of the twenty amino acids commonly found in naturally occurring proteins, and are well known in the art. These provide a substituent of the formula —NHCH-RCOOH, with R being the side chain of any of the twenty standard amino acids. The amino acids may be of any configuration, but preferably have an (L) configuration.

A compound of Formula I is produced in accordance with Scheme A below by alkyating a pyridone of Formula III with a chloromethylquinoline of Formula II to produce a compound of Formula IV, and then cyclizing the compound of Formula IV to yield the compound of Formula I.

Scheme A

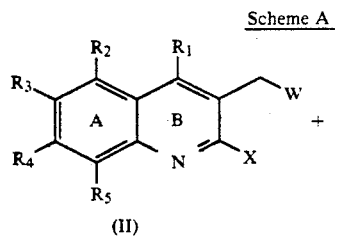

(II)

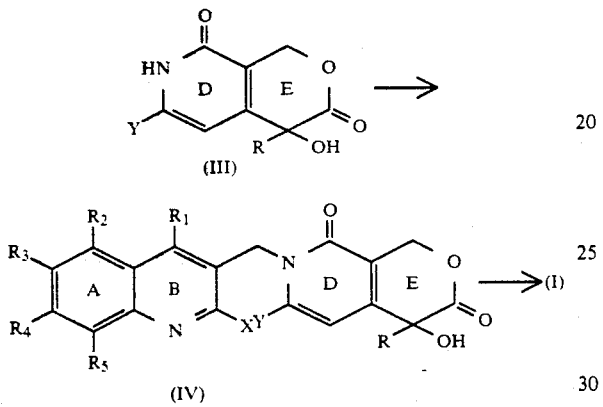

In Scheme A: Y is H; R and $R_1$ through $R_5$ are as given in connection with Formula I above; X is halogen, preferably bromo or iodo; and W is halogen, preferably chloro.

The starting materials of Scheme A, the compounds of Formula II and III, are prepared in accordance with Schemes B and C, D, or E below.

The pyridone of Formula III may be alkylated with a halomethylquinoline of Formula II in a suitable solvent, such as a polar protic solvent (e.g. isopropyl alcohol, ethanol, methanol), an aprotic solvent (e.g., 1,2-dimethoxyethane, tetrahydrofuran, toluene, acetonitrile, or dimethylformamide) or alternatively in an aqueous solution in the presence of a phase transfer catalyst. The reaction is preferably carried out under mildly basic conditions, to minimize attack on the pyridone ring oxygen. The reaction may be carried out as a single step, or may conveniently be carried out in two stages by, first, forming the anion of the pyridone by addition of an alkali earth salt (e.g., potassium tert-butoxide) at about room temperature, and then adding the halomethylquinoline to the reaction solution and heating the solution between about 60° to about 100° Centigrade for 4-24 hours.

The compound of Formula IV may be cyclized to yield the compound of Formula I by an intramolecular Heck reaction. The reaction is carried out in the presence of a palladium catalyst (e.g., palladium acetate) under basic conditions in a polar aprotic solvent such as acetonitrile or dimethylformamide. A phase transfer catalyst such as a tetraalkylammonium halide salt is preferably included. The reaction should be carried out in an inert atmosphere, such as under argon. The reaction mixture may be heated to a temperature between about 50° to about 100° C. for about 1 to 24 hours. Variations on these conditions will be apparent from the literature on the Heck reaction. See, e.g., R. Grigg et al. *Tetrahedron* 46, 4003-4008 (1990).

The compounds of Formula II may be prepared in accordance with Scheme B below, where $R_1$ through $R_5$ are as given in connection with Formula I above, and X is bromo or iodo, preferably iodo.

Scheme B

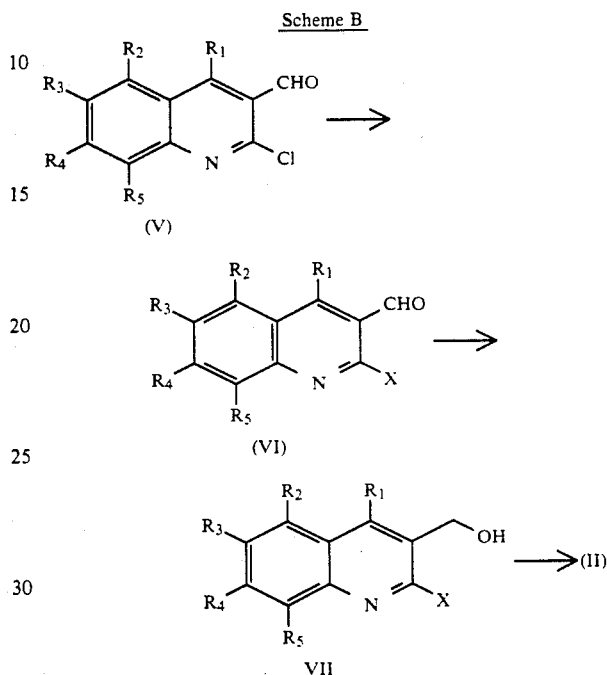

The starting materials in Scheme B, the compounds of Formula V, are made by known techniques, such as by chlorination of a quinoline. See, e.g., *Progress in Heterocyclic Chemistry* 2, 180 (H. Suschitzky and E. Scriven eds. 1990). In the alternative, eompounds of Formula V may be made from the substituted acetanilide as described by O. Meth-Coyn et al., *J. Chem. Soc. Perkin Trans.* 1 1981, 1520.

The halo group on the carboxaldehyde of Formula V is exchanged with an iodo or bromo (preferably iodo) to produce the carboxaldehyde of Formula VI. The exchange reaction may be carried out in acetonitrile in the presence of a catalytic amount of a strong acid, such as HCl, by heating the reaction mixture to between about 70° to about 90° C. for at least about 4 hours.

The carboxaldehyde of Formula VI is then reduced to produce the hydroxymethylquinoline of Formula VII. The reaction is carried out with a mild reducing agent to avoid reducing the quinoline ring, at a temperature of from about 0° to about 25° C., in an alcohol solvent. An alternative route for producing a compound of Formula VII is disclosed in N. Narasimham et al., *J. Chem. Soc., Chem. Commun.*, 1985, 1368-1369.

A compound of Formula II is produced from the hydroxymethylquinoline of Formula VII in accordance with conventional procedures in a solvent in which the reactants are soluble, such as dimethylformamide. The reaction is preferably carried out at lower temperatures to provide a higher yield.

The compounds of Formula III above are preferably prepared in accordance with Scheme C below, wherein R is as given in connection with Formula I above, $R_6$ and $R_7$ are loweralkyl, preferably methyl. $R_8$ is loweral-

Scheme C

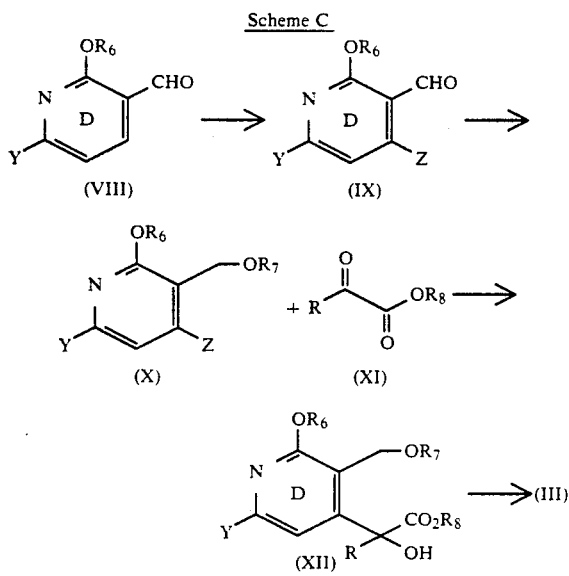

The starting materials for Scheme C, the compounds of Formula VIII, may be prepared in accordance with known techniques. For example, the synthesis of 2-methoxy-3-pyridinecarboxaldehyde is disclosed in D. Comins and M. Killpack, *J. Org. Chem.* 55, 69–73 (1990).

In Scheme C, the carboxaldehyde of Formula VIII is halogenated to produce the 4-halo-3-pyridinecarboxaldehyde of Formula IX. Halogenation at the 4- position may be carried out by reacting the carboxaldehyde of Formula VIII with a lithiated diamine, such as lithiated N,N,N'-trimethylethylenediamine, in dimethoxyethane or tetrahydrofuran to protect the aldehyde and direct subsequent C-4 lithiation, and by then lithiating the C-4 position of the pyridine with a suitable lithiating reagent, such as n-butyllithium. See D. Comins and M. Killpack, supra. The C-4 lithiated pyridine intermediate is preferably halogenated by adding the intermediate to a solution of iodine or bromine in a polar or nonpolar organic solvent, preferably at a temperature of at least as low as about $-70°$ C.

The compound of Formula IX is reduced in an alcoholic acidic media in the presence of a trialkylsilane to yield the alkoxymethylpyridine of Formula X. The acid should be a strong acid, such as sulfuric or trifluoroacetic acid. At least about 2 molar equivalents of a suitable alcohol (e.g., methanol, ethanol, tert-butanol] should be included to convert the aldehyde to the ether. Reference may be made to the literature on the silane reduction of aldehydes for conditions and variations on this reaction. See, e.g., M. Doyle et al., *J. Am. Chem. Soc.* 94:10, 3659–3661 (1972).

The compound of Formula X is lithiated at the C-4 position with a lithiating agent such as n-butyllithium, and then reacted with a compound of Formula XI such as an alkyl α-ketobutyrate (e.g., methyl α-ketobutyrate, ethyl α-ketobutyrate, tert-butyla-ketobutyrate) to produce the compound of Formula XII in essentially the manner described by R. Lyle et al., *J. Org. Chem.* 38, 3268–3271 (1973). The reaction may be carried out in a tetrahydrofuran or ether solvent at a temperature of at least as low as about $50°$ C., with the alkyl α-ketobutyrate being added to the reaction solution as a single aliquot.

The compound of Formula XII is then cyclized to yield the compound of Formula III. Cyclization may be carried out by reacting the compound of Formula XII with bromo- or iodotrimethylsilane (preferably iodotrimethylsilane) in a neutral or polar aprotic solvent such as acetonitrile, followed by reaction with a strong acid solution to cleave the ethers and yield the compound of Formula III (the ring forming spontaneously upon cleavage of the ethers). The bromo- or iodotrimethylsilane is preferably generated in situ in accordance with known techniques, such as by the reaction of chlorotrimethylsilane with a halogen salt or elemental halogen. See A. Schmidt, *Aldrichimica Acta* 14, 31–38 (1981).

When Y is halo in the compound of Formula III, the compound may be hydrogenated by any suitable technique, preferably by catalytic hydrogenation in the presence of a palladium catalyst in a hydrogen atmosphere under pressure (e.g., at least three atmospheres). See generally J. March, *Advanced Organic Chemistry*, 510–511 (3d. Ed. 1985).

As alternatives to Scheme C, a compound of Formula III, where Y is H, may be prepared in the manner described in D. Comins, Ph.D. Thesis, University of New Hampshire, Durham. N.H., at 25–29 (1977), and as described in Lyle et al., *J. Org. Chem.* 38, 3268–3271 (1973).

Another alternative to Scheme C is Scheme D, shown below,

Scheme D

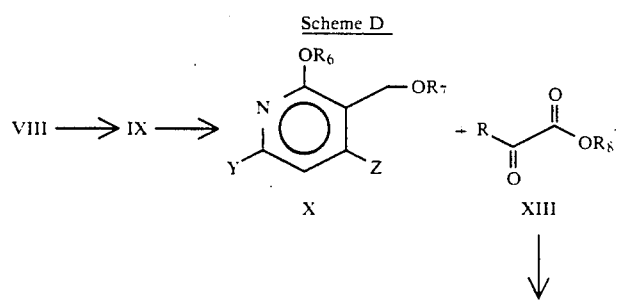

Scheme D

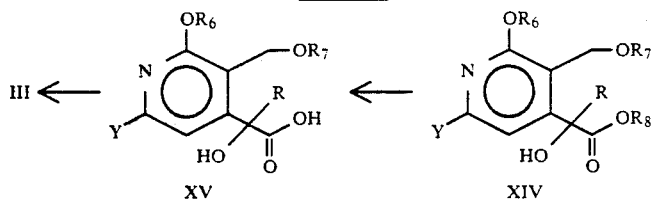

wherein R, $R_6$, $R_7$, Y, and Z are as given in connection with Formula III above. $R_8$ can be any chiral moiety which, because of its geometric configuration, directs the nucleophilic substitution of compound XIII by compound X to preferentially form the tertiary alcohol of compound XIV in one stereochemical orientation over its opposite stereochemical orientation. $R_8$ forces a preferential orientation of compound XIV by sterically hindering the formation of the non-preferred diastereomer. Exemplary chiral compounds suitable for use in the process include aryl and alkyl aryl compounds optionally substituted from 1 to 5 times with C1-C4 alkyl groups, any of the compounds disclosed in U.S. patent application Ser. No. 07/855,721, the subject matter of which is herein incorporated by reference, 4-phenylmethyl -2 oxazolidine, 3-(1-naphthyl)-4,7,7-trimethylbicyclo [2.2.1] heptane, trans-2,5 Bis(methoxymethoxy methyl)pyrrolidine, 2,10-camphorsulfamide, N,N-dicylcohexyl-10 camphorsulfamide, proline benzyl ester, pantolactone, and 4-benzyl-Z-oxazolidinone. Preferred chiral auxiliaries are compounds of the Formula XVIII

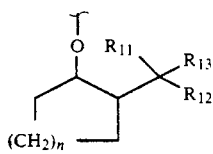

(XVIII)

wherein n is 1, 2, or 3, $R_{11}$ is C1-C4 alkyl, $R_{12}$ is the same C1-C4 alkyl group as $R_{11}$, or $R_{11}$ and $R_{12}$ together form cyclopentane or cyclohexane, and $R_{13}$ is selected from the group consisting of phenyl, naphthyl, anthryl, or phenanthryl optionally substituted from 1 to 5 times with $C_3$-$C_7$ secondary alkyl or $C_4$-$C_7$ tertiary alkyl groups. The position of alkyl substituents on the aryl group is not critical; for example, phenyl can be substituted at positions 1-6, naphthyl from positions 1-8, anthryl from positions 1-10, and phenanthryl from positions 1-10 substituted from 1 to 5 times with C1-C4 alkyl groups. It is understood that the oxygen atom illustrated in XVIII links the chiral auxiliary to the carbonyl carbon of compound XIII and is included in the Formula XVIII to indicate the preferred bonding position of the cyclic alkyl group that carbonyl carbon. In a more preferred chiral auxiliary, $R_{11}$ and $R_{12}$ are both methyl or ethyl, and $R_{13}$ is phenyl.

In many instances it will be desirable that compound XIV has the stereochemical orientation of Formula (XIVa).

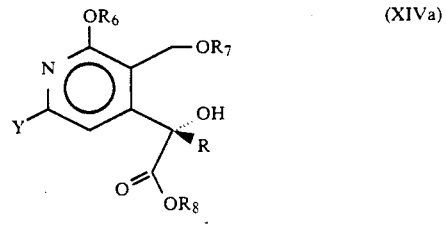

(XIVa)

In such instances, $R_8$ should be an optically pure chiral auxiliary that will permit only the formation of diastereomers of compound XIV having this orientation. As used herein, an "optically pure" compound is one which contains at least 99 percent of one enantiomer of that compound. Preferred chiral auxiliaries for forming the diastereomers of Formula XIVa are as shown in Formula XVIIIa

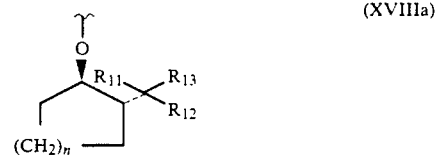

(XVIIIa)

wherein R, $R_{11}$, $R_{12}$, and $R_{13}$ are as defined for Formula VIII. As above, the oxygen atom of compound XVIIIa is included to show bonding position on the cyclic alkyl group and stereochemical orientation of the substituents thereon.

Scheme D proceeds in the same manner as Scheme C through the synthesis of compound X. At that point compound X is dehalogenated with a base of the formula $A^+B^-$, wherein $A^+$ is an inorganic cation, and $B^-$ is an organic anion, to form an intermediate, then reacting that intermediate with an α-ketoester of Formula XIII to form a compound of Formula XIV.

The base $A^+B^-$ can be any combination of an inorganic cation and an organic anion which will remove Z from compound X to form a reactive carbanion intermediate. Exemplary inorganic cations include sodium, potassium, and lithium, with lithium being more preferred. The organic anion can be any anion which is sufficiently basic to remove substituent Z from compound X but is insufficiently strong to remove substituent Y from compound X. Exemplary organic anions include propyl, n-butyl, t-butyl, phenyl, and n-pentyl, with n-butyl being preferred.

The reaction step in which Z is removed from compound X can be carried out through the use of standard conditions for removing halogens from aromatic compounds. Preferably, this step is carried out in an inert atmosphere, such as argon or nitrogen, and in an aprotic solvent, such as tetrahydrofuran, diethyl ether, dimethoxyethane, and toluene, with tetrahydrofuran being preferred. The reaction is preferably carried out at a reduced temperature, and more preferably is carried out at below 0° C.

The combination of the intermediate produced by reaction with base A+B− and the α-ketoester of formula XIV can be carried out through the use of standard conditions for nucleophilic attack of an aromatic carbanion at an α-carbonyl carbon. Preferably, the reaction is carried out in an aprotic solvent, such as those listed above, with tetrahydrofuran being preferred, and is carried out at a reduced temperature, preferably below 0° C. In a more preferred embodiment of the process, the reacting step and the combining step are carried out in the same reaction vessel, i.e, in situ.

lane. Exemplary amines are secondary and tertiary amines, with 1,8-diazabicyclo[5,4,0]undec-7-ene being preferred. The ethers can be cleaved by conventional methods, such as those described above in Scheme C for producing compound III from compound XII. The process is preferably carried out in an aprotic solvent, such as acetonitrile, tetrahydrofuran, or diethylether. Also, the process is preferably conducted so that the reacting step and the cyclizing step are carried out in the same reaction vessel, i.e., in situ.

Alternatively, a compound of the Formula XV can be made by Scheme E from a compound of Formula X. Scheme E is shown below.

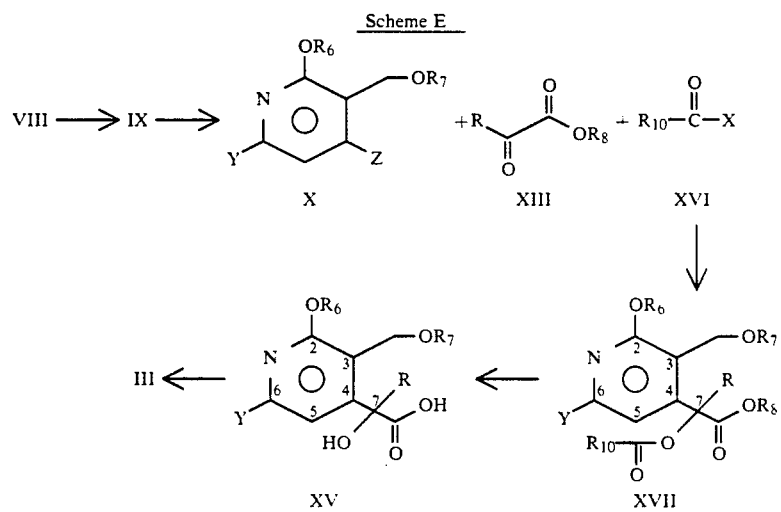

Proceeding stepwise through Scheme D, a compound of Formula XV can then be prepared by saponifying a compound of Formula XIV with a base to form an intermediate, then protonating the intermediate with aqueous acid.

The saponification step can be carried out under any conditions that are known for saponifying esters to carboxylic acids. Preferably, the saponifying base used is a mixture of an inorganic base, such as sodium hydroxide or potassium hydroxide, and a relatively polar organic solvent, such as ethanol. The protonating step can be carried out with any aqueous acid solution, such as hydrochloric or sulfuric acid, that will protonate the carboxylate anion resulting from saponification of the ester linkage of compound XIV.

Preferably, the process is carried out so that after the saponification step, but prior to the protonating step, the chiral auxiliary ($R_8$) can be recovered in good yield for re-use. This can be performed by any method of recovery known to be suitable for compounds of this type. Preferably, the basic solution remaining from the saponification is washed with a non-polar, aprotic solvent, such as dimethyl ether or diethyl ether, which extracts the chiral auxiliary $R_8$ from solution.

The final step of Scheme D is the formation of Compound III from a compound of Formula XV. This process comprises the steps of reacting compound of Formula XV with a halotrialkylsilane in the presence of an alkyl or aryl amine to form an intermediate, then cyclizing the intermediate by hydrolysis of the reaction product in aqueous acid to cleave the ether linkage of $R_6$ and $R_7$, the ring forming spontaneously upon ether cleavage. A preferred halotrialkylsilane is iodotrimethylsi- R, $R_6$, $R_7$, and $R_8$ are as given above for Scheme D. $R_{10}$ can be any aryl, alkyl, or alkyl aryl group which will cause the compound of Formula XVII to recrystallize and separate from the undesired minor diastereomer. $R_{10}$ is preferably selected from the group consisting of biphenyl, anthryl, phenanthryl, and phenyl, any of which can be substituted from 1 to 5 times with C1–C4 alkyl groups. The position of alkyl substituents on the aryl group is not critical; for example, phenyl can be substituted at positions 1–6, naphthyl from positions 1–8, anthryl from positions 1–10, and phenanthryl from positions 1–10 substituted from 1 to 5 times with C1–C4 alkyl groups. More preferably, $R_{10}$ is biphenyl. X is selected from the group consisting of chlorine, bromine, and iodine.

Scheme E represents a process comprising the steps of reacting a compound of Formula X with a base A+B− to form first intermediate, combining the intermediate with an α-ketoester containing a chiral auxiliary of Formula XIII to form a second intermediate, the alkoxide of compound XIV, then acylating this second intermediate with a compound of Formula XVI to form a compound of Formula XVII.

This scheme differs from Scheme D only in that another acylation step is included for the formation of an additional ester linkage at the hydroxyl group attached to the chiral carbon at position 7. The purpose of the additional substituent $R_{10}$ is to form a compound that can be separated easily from solution by recrystallization. Without this step, it can be difficult to separate the compound of Formula XIV from a minor diastereomer by-product of the reaction; this is problematic if, as is often the case when chiral auxiliaries are used in synthetic reactions, a diastereomerically or optically pure product is desired. By including in compound XVII the ester linking R$_{10}$ to compound XIV, the reaction product XVII can be purified by standard recrystallization methods, such as precipitation from an organic solvent, to produce a diastereomerically pure compound XVII. As used herein, "diastereomerically pure" means that a compound sample comprises at least 99 percent of one of at least two possible diastereomers. This diastereomerically pure compound XVII can in turn be used to produce an optically pure compound XV, which in turn can be used to produce an optically pure compound III.

Scheme E proceeds in the manner described above in Scheme D for the preparation of Compound XIV. Once compound XIV has been prepared, the acylation step can be carried out in any manner known for acylating tertiary alcohols with acyl halides. In a preferred embodiment, R$_{10}$ is added to a reaction mixture in which compound XIV has been prepared in its alkoxide form, so that the reaction proceeds in situ. The solvent should be an aprotic solvent, such as tetrahydrofuran, diethyl ether, dimethoxyethane, or toluene, with tetrahydrofuran being preferred. Preferably the reaction occurs in an inert atmosphere, such as under argon or nitrogen. The reaction product is separated from the reaction mixture, preferably by recrystallization, for use in subsequent steps. If an optically pure chiral axillary R$_8$ was used, the recrystallized compound XVII will contain only one disastereomer, the diastereomer having a stereochemical orientation of the substituents of the chiral carbon 7 of compound XVII directed by the chiral auxiliary. A preferred orientation at chiral carbon atom 7 is shown in Formula XVIIa.

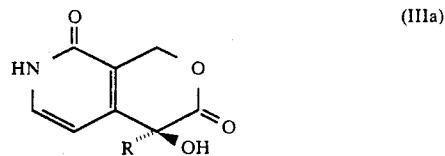

(XVIIa)

which can be produced by use of an optically pure compound of Formula XIIIa. Any further synthetic process that includes compound XVIIa will then produce reaction products having the same stereochemical orientation at chiral carbon 7.

From this point, Scheme E parallels Scheme D. Compound XVII is saponified with a base to form an intermediate, then the intermediate is protonated to form a compound of Formula XV. As was true for the saponifying step of Scheme D, this step of Scheme E can be carried out with any base that will cleave the ester linkages bonding R$_8$ and R$_{10}$ to compound XVII. Preferably, the base is a mixture of a relatively polar organic solvent, such as ethanol, and an inorganic aqueous base, such as sodium hydroxide. After the saponifying base cleaves both ester linkages present in compound XVII to form the carboxylate and alkoxide form of the compound, the protonating acid then protonates these functional groups to form a compound of Formula XV. As in Scheme D, the chiral auxiliary can be recovered after saponification for re-use by nonpolar solvent washing or some other suitable technique.

The final step of Scheme E is the cyclizing of compound XV to compound III. The same reaction conditions listed above for Scheme D are suitable here. As indicated above, the compound can be made in an optically pure form by using an optically pure chiral auxiliary R$_8$ in Scheme E; a preferred stereochemical orientation is shown in Formula IIIa,

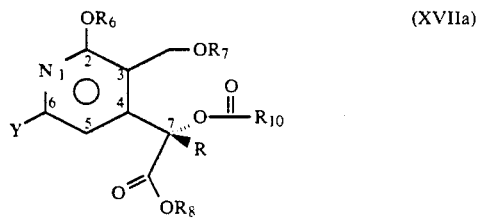

(IIIa)

which can be made from the diastereomerically pure form of compound XVIIa after saponification to an optically pure form of compound XVa.

Specific examples of compounds which may be prepared by the method of the present invention include 9-methoxy-camptothecin, 9-hydroxy-camptothecin, 9-nitro-camptothecin, 9-amino-camptothecin, 10-hydroxy-camptothecin, 10-nitro-camptothecin, 10-amino-camptothecin, 10-chloro-camptothecin, 10-methyl-camptothecin, 11-methoxy-camptothecin, 11-hydroxy-camptothecin, 11-nitro-camptothecin, 11-amino-camptothecin, 11-formyl-camptothecin, 11-cyano-camptothecin, 12-methoxy-camptothecin, 12-hydroxy-camptothecin, 12-nitro-camptothecin, 10,11-dihydroxy-camptothecin, 10,11-dimethoxy-camptothecin, 7-methyl-10-fluoro-camptothecin, 7-methyl-10-chloro-camptothecin, 7-methyl-9,12-dimethoxy-camptothecin, 9,10,11-trimethoxy-camptothecin, 10,11-methylenedioxy-camptothecin and 9,10,11,12-tetramethyl-camptothecin.

Compounds of Formula I have antitumor and antileukemic activity. Additionally, compounds of Formula I wherein R$_1$ is halo are useful as intermediates for, among other things, making compounds of Formula I wherein R$_1$ is loweralkyl.

Those skilled in the art will appreciate that additional changes can be made in the compounds of Formula I (see, for examples, J. Cai and C. Hutchinson, supra), which changes will not adversely affect the new processes disclosed herein and do not depart from the concept of the present invention.

In the Examples which follow, "mg" means milligrams, "g" means grams, "M" means Molar, mL means millimeter(s), "mmol" means millimole(s), "Bu" means butyl, "THF" means tetrahydrofuran, "h" means hours, "min" means minutes, "C" means Centigrade, "p.s.i." means pounds per square inch, "DMF" means dimethylformamide, "TLC" means thin layer chromatography, and "PLC" means preparative thin layer chromatography.

EXAMPLE 1

6-Chloro-2-methoxy-3-pyridinecarboxaldehyde

To a solution of tert-butyllithium (1.7M in pentane, 48.5 mL, 83.0 mmol) in 150 mL of THF at −78° C. was added 6-chloro-2-methoxypyridine (8.94 mL, 75.0 mmol) over 5 min. The reaction mixture was stirred at −78° C. for 1 h, then dimethylformamide (7.55 mL, 97 mmol) was added and the mixture was stirred at this temperature for 1.5 h. After the addition of glacial acetic acid (8.6 mL, 150 mmol), the reaction mixture was allowed to warm to room temperature over a 30-min period, then diluted with ether (200 mL). The organic phase was washed with saturated aqueous NaHCO$_3$ (100 mL) and brine (100 mL), and was dried over MgSO$_4$. Concentration afforded the crude product as a light yellow solid which was recrystallized from hexanes to give 9.6 g (75%) of 6-chloro-2-methoxy-3-pyridinecarboxaldehyde as a white solid: mp 80°-81° C. (mp 62°-64° C.) (See Dainter, R. S.; Suschitzky, H.; Wakefield, B. J. Tetrahedron Lett. 1984, 25, 5693.). $^1$H NMR (300 MHz, CDCl$_3$) δ10.31 (s,1H), 8.07 (d, 1H, J=9 Hz), 7.03 (d, 1H, J=9 Hz), 4.09 (s, 3H); IR (nujol) 1685, 1580, 1565, 1270, 1140, 1090, 1005, 905, 820, 755 cm$^{-1}$.

EXAMPLE 2

6-Chloro-4-iodo-2-methoxy-3-pyridinecarboxaldehyde

To a solution of N,N,N'-trimethylethylenediamine (2.46 mL, 19.23 mmol) in 15 mL of 1,2-dimethoxyethane at −23° C. was added n-BuLi (9.22 mL, 19.23 mmol), and the solution was stirred at −23° C. for 20 min. The mixture was transferred using a double-tipped needle to a solution of 6-chloro-2-methoxy-3-pyridinecarboxaldehyde (3.0 g, 17.5 mmol) in 40 mL of 1,2-dimethoxyethane at −23° C. After stirring for 15 min, n-BuLi (12.6 mL, 26.2 mmol) was added and the dark mixture was stirred an additional 2 h at −23° C. The solution was transferred using a double-tipped needle to a solution of iodine (8.04 g, 31.7 mmol) in 40 mL of 1,2-dimethoxyethane at −78° C. After stirring at −78° C. for 30 min, the cooling bath was removed and the reaction mixture was allowed to warm for 20 min, then quenched with water. The mixture was extracted with ether (2×30 mL) and the combined organic layers were washed successively with 30-mL portions of 10% aqueous Na$_2$S$_2$O$_3$, water and brine, and dried over MgSO$_4$. Concentration afforded 4.62 g (89%) of crude product to which was added 50 mL of hexanes. The mixture was stirred and allowed to stand at 5° C. overnight. Filtration gave 2.67 g of 6-chloro-4-iodo-2-methoxy-3-pyridinecarboxaldehyde as a yellow solid: mp 120°-124° C. Concentration of the hexane washings and purification of the residue by radial preparative thin-layer chromatography (silica gel, 5% ethyl acetate/hexanes) gave an additional 1.41 g of product (mg 120°-124° C.), raising the total yield of the compound to 78%. Recrystallization from hexanes gave an analytical sample as a bright yellow solid: mp 129°-130° C. $^1$H NMR (300 MHz, CDCl$_3$) δ 10.16 (s, 1H), 7.59 (s, 1H), 4.07 (s, 1H); IR (nujol) 1690, 1350, 1260, 1095, 1010, 900, 840 cm$^{-1}$.

EXAMPLE 3

2-Chloro-4-iodo-6-methoxy-5-(methoxymethyl)pyridine

To a mixture of 6-chloro-4-iodo-2-methoxy-3-pyridinecarboxaldehyde (1.07 g, 3.60 mmol), triethylsilane (0.86 mL, 5.40 mmol) and methanol (0.43 mL, 10.6 mmol) at 0° C. was added trifluoroacetic acid (2.2 mL, 28.6 mmol), and the resulting solution was stirred at 25° C. for 14 h. After dilution with ether (30 mL), saturated NaHCO$_3$ was added until the aqueous phase was rendered basic. The aqueous layer was extracted with ether (10 mL), and the combined ether layers were washed with water (10 mL) and brine (10 mL), and dried (Na$_2$SO$_4$). Concentration gave the crude product which was purified by radial PLC (silica gel, 5% ethyl acetate/hexanes) to afford 2-chloro-4-iodo-6-methoxy-5-(methoxymethyl)pyridine as a white solid (1.05 g, 93%): mp 69°-72° C. Recrystallization from hexanes provided an analytical sample: mp 74°-75° C. $^1$H NMR (300 MHz, CDCl$_3$) δ 7.40 (S, 1H). 4.53 (s, 2H), 3.96 (s, 3H), 3.42 (s, 3H); IR (nujol) 1550, 1300, 1115 1090, 1020, 940, 905, 830, 720 cm$^{-1}$.

EXAMPLE 4

Ethyl 2-hydroxy-2-(6'-chloro-2'-methoxy-3'-methoxymethyl-4'-pyridyl)butyrate

To a solution of 2-chloro-4-iodo-6-methoxy-5-(methoxymethyl)pyridine (2.28 g, 7.30 mmol) in 50 mL of THF at −90° C. was added n-BuLi (3.46 mL, 8.03 mmol) over 5 min and the resulting solution was stirred at −90° C. for 30 min. Ethyl α-ketobutyrate (1.25 mL, 9.45 mmol) was added, the reaction mixture was stirred at −90° C. for 30 min, then allowed to warm at ambient for 20 min, and quenched with saturated NH$_4$Cl. After removal of most of the solvent under reduced pressure, the residue was taken up in 40 mL of ether, washed with dilute NaHCO$_3$ (15 mL) and brine (15 mL), and was dried over MgSO$_4$. Evaporation of the solvent in vacuo and purification of the residue by radial PLC (10% acetone/hexanes) afforded ethyl-2-hydroxy-2-(6'-chloro-2'-methoxy-3'-methoxymethyl-4'-pyridyl)butyrate (1.53 g, 66%) as a light yellow, viscous oil. $^1$H NMR (300 MHz, CDCl$_3$) δ 7.07 (s, 1H), 4.75 (d, 1H, J=12 Hz), 4.47 (d, 1H, J=12 Hz), 4.24 (q, 1H, J=6 Hz), 4.17 (q, 1H, J=6 Hz), 3.96 (s, 3H), 3.37 (s, 3H), 2.16 (m, 2H), 1.24 (t, 3H, J=6 Hz); IR (film) 3400, 1735, 1580, 1555, 1305, 1235, 1130, 1090, 1020, 905, 830, 730 cm$^{-1}$.

EXAMPLE 5

9-Chloro-7-oxopyrido[5,4-c]-2-oxo-3-ethyl-3-hydroxy-3,6-dihydropyran

To a stirred mixture of the hydroxy ester prepared in Example 4 above (1.53 g, 4.82 mmol) and sodium iodide (2.89 g, 19.3 mmol) in dry CH$_3$CN (35 mL) at 25° C. was added dropwise chlorotrimethylsilane (2.45 mL, 19.3 mmol). The resulting solution was heated at reflux for 4 h, the solvent was removed under reduced pressure, and 100 mL of 5N HCl was added to the residue. After heating at a gentle reflux for 4 h, the mixture was stirred at 25° C. overnight, then extracted with six 30-mL portions of CHCl$_3$ containing 5% CH$_3$OH. The combined organic extracts were washed with 40 mL of half-saturated NaCl containing Na$_2$S$_2$O$_3$, followed by 40 mL of saturated NaCl. After drying over Na$_2$SO$_4$, the solvent was removed under reduced pressure and the residue was purified by radial PLC (silica gel, 5% CH$_3$OH/CHCl$_3$) to give 9-chloro-7-oxopyrido[5,4-c]-2-oxo-3-ethyl-3-hydroxy-3,6-dihydropyran (743 mg, 63%) as an off-white solid: mp 205°-207° C. Recrystallization from CHCl$_3$/CH$_3$OH gave an analytically pure sample as a white solid: mp 207°-208° C. $^1$H NMR (300 MHz, CDCl$_3$DMSO-d6) δ 6.79 (s, 1H), 5.49 (d, 1H, J=15 Hz), 5.13 (d, 1H, J=15 Hz), 1.78 (q, 2H, J=6 Hz), 0.93 (t, 3H, J=9 Hz), IR (nujol) 3450, 1740, 1640, 1600, 1560, 1320, 1225, 1140, 1035, 995, 940 cm$^{-1}$.

EXAMPLE 6

7-Oxopyrido[5,4-c]-2-oxo-3-ethyl-3-hydroxyl-3,6-dihydropyran

A mixture of the chloropyridone prepared in Example 5 above (400 mg, 1.64 mmol) and sodium acetate (400 mg, 4.86 mmol) in 25 mL of ethanol was hydrogenated over 10% Pd/C (100 mg) at 42 psi for 4 h. The mixture was filtered through celite and the solids were washed with $CH_3OH$. The filtrate was concentrated and the residue was purified by radial PLC (silica gel, 5% $CH_3OH/CHCl_3$) to give the pure product (256 mg, 75%) as a white solid: mp 230°–232° C. (dec.). Recrystallization from $CHCl_3/CH_3OH$ afforded an analytical sample: mp 232° C. (dec.). $^1H$ NMR (300 MHz, $CHCl_3/DMSO$-d6) δ 7.30 (d, 1H, J=6 Hz), 6.49 (d, 1H, J=6 Hz), 5.42 (d, 1H, J=18 Hz), 5.12 (d, 1H, J=18 Hz), 1.79 (m, 2H), 0.91 (t, 3H, J=6 Hz); IR (nujol) 3300, 1750, 1640, 1620, 1555, 1065, 1030, 995, 805 $cm^{-1}$.

EXAMPLE 7

2-Chloro-3-quinolinecarboxaldehyde

To a solution of 0.46 mL (3.30 mmol) of diisopropylamine in 8 mL of THF at 0° C. was added 1.53 mL (3.30 mmol) of n-BuLi dropwise. After 20 min the solution was cooled to −78° C. and 2-chloroquinoline (491 mg, 3.0 mmol) was added neat. The mixture was stirred at −78° C. for 30 min, then dimethylformamide (0.39 mL, 5.04 mmol) was added dropwise and the reaction mixture was stirred an additional 30 min at this temperature. After quenching at −78° C. with glacial acetic acid (1 mL), the mixture was warmed to room temperature and diluted with ether (30 mL). The organic phase was washed with saturated $NaHCO_3$ solution (10 mL) and brine (10 mL), and was dried over $MgSO_4$. Concentration afforded 2-chloro-3-quinolinecarboxaldehyde (530 mg, 92%) as a light yellow solid (mp 145°–149° C.), which was used directly in the next step without further purification. Recrystallization from ethyl acetate afforded the pure compound as light yellow needles: mp 149°–150° C. (mp 148°–149° C. reported in Meth-Cohn, O.; Narhe, B.; Tarnowski, B. J. Chem. Soc. Perkin Trans. I 1981, 1520.). $^1H$ NMR (300 MHz, $CDCl_3$) δ 10.57 (s, 1H), 8.77 (s, 1H), 8.08 (d, 1H, J=9 Hz), 8.0 (d, 1H, J=9 Hz), 7.90 (d, 1H, J=9 Hz), 7.67 (t, 1H, J=9 Hz); IR (nujol) 1685, 1575, 1045, 760, 745 $cm^{-1}$.

EXAMPLE 8

Preparation of 2-Chloro-3-quinolinecarboxaldehyde from acetanilide

Following a literature procedure (see Meth-Cohn, O.; Narhe, B.; Tarnowski, B. J. Chem. Soc. Perkin Trans. I 1981, 1520), a phosphorus oxychloride (24.0 mL, 260 mmol) was added dropwise to an ice-cold solution of dimethylformamide (7.20 mL, 93.0 mmol) and the deep-red solution was stirred at 0° C. for 30 min. Acetanilide (5.0 g, 37.0 mmol) was added neat and the mixture was stirred at 0° C. for 30 min., then heated at 75° C. for 16 h. The cooled mixture was poured into 250 mL of ice-water and stirred at 0°–5° C. for 30 min. The product was filtered, washed with water, and recrystallized from ethyl acetate to give 5.2 g (74%) of 2-chloro-3-quinoline-carboxaldehyde as a light yellow solid: mp 147°–149° C.

EXAMPLE 9

2-Iodo-3-quinolinecarboxaldehyde

A mixture of the aldehyde prepared in accordance with Example 7 or 8 above (5.0 g, 26.2 mmol), sodium iodide (10.0 g, 66.7 mmol) and concentrated HCL (1 mL) in 100 mL of $CH_3CN$ was heated at reflux for 4.5 h. After removal of most of the solvent in vacuo, aqueous $Na_2CO_3$ was added until the mixture was basic, and the product was filtered and washed with water. The crude product was recrystallized from 95% ethanol to give 6.51 g (88%) of 2-iodo-3-quinolinecarboxaldehyde as off-white fluffy needles: mp 156°–157° C. (mp 150°–152° C. reported in Meth-Cohn, O.; Narhe, B.; Tranowski, B.; Hayes, R.; Keyzad, A.; Rhavati, S.; Robinson, A. J. Chem. Soc. Perkin Trans. I 1981, 2509). $^1H$ NMR (300 MHz, $CHCl_3$) δ 10.29 (s, 1H), 8.57 (s, 1H), 8.12 (d, 1H, J=9 Hz), 7.98 (d, 1H, J=9 Hz) 7.88 (t, 1H, J=9 Hz), 7.68 (t, 1H, J=9 Hz); IR (nujol) 1680, 1610, 1570, 1555, 1315, 1020, 1005, 750, 740 $cm^{-1}$.

EXAMPLE 10

3-Hydroxymethyl-2-iodoquinoline

To a stirred solution of 2-iodo-3-quinolinecarboxaldehyde (595 mg, 2.10 mmol) in 40 mL of $CH_3OH$ at 0° C. was added $NaBH_4$ (86 mg, 2.31 mmol), and the mixture was stirred at 0° C. for 30 min. After concentrating the mixture to approximately one-half of its original volume, water (30 mL) was added and the mixture was allowed to stand at 5° C. overnight. The solids were filtered and the crude product (570) mg, 95%) was recrystallized from methanol to give 3-hydroxymethyl-2-iodoquinoline (505 mg, 84%) as colorless needles: mp 189°–190° C. $^1H$ NMR (300 MHz, $CDCl_3$) δ 8.19 (s, 1H), 7.99 (d, 1H, J=9 Hz), 7.87 (d, 1H, J=9 Hz), 7.68 (m, 1H), 7.58 (t, 1H, J=9 Hz), 5.45 (t, 1H, J=6 Hz), 4.66 (d, 2H, J=6 Hz); IR (nujol) 3350, 1580, 1320, 1125, 1060, 995, 755, 720, $cm^{-1}$.

EXAMPLE 11

3-Chloromethyl-2-iodoquinoline

To a stirred mixture of 3-hydroxymethyl-2-iodoquinoline prepared in accordance with Example 10 above (350 mg, 1.23 mmol) and triphenylphosphine (483 mg, 1.84 mmol) in 10 mL of dry DMF at −23° C. was added N-chlorosuccinimide (246 mg, 1.84 mmol), and the mixture was stirred for 1 h at −23° C. After the addition of 40 mL of dilute aqueous $NaHCO_3$, the mixture was extracted with ethyl acetate (20 mL) and then ether (2×15 mL). The combined organic extracts were washed successively with 20-mL portions of dilute $NaHCO_3$, water and brine, and were dried over $MgSO_4$. Concentration and purification of the residue by radial PLC (silica gel, 10% ethyl acetate/hexanes) afforded 312 mg (84%) of 3-chloromethyl- 2-iodoquinoline as a white crystalline solid: mp 138°–140° C. Recrystallization from hexanes afforded an analytical sample as colorless needles: mp 139°–140° C. $^1H$ NMR (300 MHz, $CDCl_3$) δ 8.17 (s, 1H), 8.07 (d, 1H, J=9 Hz), 7.84 (d, 1H, J=9 Hz), 7.75 (t, 1H, J=9 Hz), 7.62 (t, 1H, J=9 Hz), 4.80 (s, 1H); IR (nujol) 1585, 1555, 1260, 1010, 780, 755, 710 $cm^{-1}$.

EXAMPLE 12

8-(21-Iodo-3'-quinolylmethyl)-7-oxopyrido[5,4-c]-2-oxo-3-ethyl-3-hydroxy-3, 6-dihydropyran To a solution containing 45 mg (0.40 mmol) of potassium tert-butoxide in 4 mL of dry isopropyl alcohol at 25° C. was added 55 mg (0.26 mmol) of 7-oxopyrido[5,4-c]-2-oxo-3-ethyl-3-hydroxy-3, 6-dihydropyran prepared in accordance with Example 6 above and the mixture was stirred at 25° C. for 30 min. A solution of 3-chloromethyl-2-iodoquinoline prepared in accordance with Example 11 above (104 mg, 0.35 mmol) in 1 mL of $CH_3OH$ was added dropwise to the white suspension, and the resulting solution was heated at 75° C. for 24 h. After quenching the reaction mixture with saturated NH4Cl, the solvents were removed under reduced pressure, and the residue was taken up in CH2Cl2 (20 mL) and washed with brine (2×10 mL). Concentration and purification of the residue by radial PLC (2% CH3OH/CHCl3) gave the product (99 mg, 80%) as a white solid: mp 171°–174° C. (dec.). Recrystallization from ethyl acetate/hexanes afforded an analytical sample: mp 174° C. (dec.). $^1$H NMR (300 MHz, CDCl3) δ 8.05 (d, 1H, J=9 Hz), 7.70–7.80 (m, 3H), 7.55–7.61 (m, 2H), 6.61 (d, 1H, J=9 Hz), 5.63 (d, 1H, J=15 Hz), 5.43 (d, 1H, J=15 Hz), 5.27 (d, 1H, J=9 Hz), 5.22 (d, 1H, J=9 Hz); IR (nujol) 3350, 1750, 1650, 1590, 1565, 1160, 1140, 1000, 750 cm$^{-1}$.

EXAMPLE 13

(±)-Camptothecin

A mixture of 8-(2'-iodo-3'-quinolylmethyl)-7-oxopyrido[5,4-c]-2-oxo-3-ethyl-3-hydroxy-3,6-dihydropyran prepared in accordance with Example 12 above (76 mg, 0.16 mmol), K2CO3 (44 mg, 0.32 mmol), tetrabutylammonium bromide (52 mg, 0.16 mmol) and Pd(OAc)2 (3.6 mg, 0.016 mmol) in 15 mL of dry acetonitrile under argon was heated at 90° C. for 5 h. TLC analysis of the reaction mixture showed a single spot which was highly U.V. active. The mixture was cooled, concentrated, and the residue was taken up in 30 mL of CHCl3 containing 10% CH3OH. This was washed with two 10-mL portions of saturated aqueous NH4Cl. The organic layer was dried over Na2SO4 and concentrated. The dark residue was subjected to radial PLC (silica gel, 4% CH3OH/CHCL3), to give 17 mg of an orange solid which was shown by NMR analysis to be a mixture of impure (±)-camptothecin and tetrabutylammonium bromide. The aqueous washings were filtered to give a yellow solid which was purified by radial PLC (silica gel, 4% CH3OH/CHCl3) to afford (±)-camptothecin (26 mg, 47%) as a yellow solid: mp 275°–277° C. (mp 275°–277° C. reported in Volman, R.; Danishefsky, S.; Eggler, J.; Soloman, D. M., J. Am. Chem. Soc. 1971, 93, 4074.).

EXAMPLE 14

Synthesis of (1R,4S,5R)-8-phenylmenthyl-(S)-2-(4-phenylbenzoyloxy)-2-(6'-chloro-2'-methoxy-3'-methoxymethyl-4'-pyridyl)butyrate n-BuLi (1.86 M, 2.72 mL, 5.05 mmol) was added to a vigorously stirred solution of 6-chloro-4-iodo-3-methoxymethyl-2-methoxypyridine (1.51 g, 4.81 mmol) in 30 mL of THF at −78° C. under Ar, and the mixture was stirred for 1 min. A solution of (−)-8-phenylmenthyl 2-ketobutyrate (1.60 g, 5.29 mmol) in 3 mL of THF was added. The reaction mixture was stirred at −78° C. for 1 h after which a solution of 4-biphenylcarbonyl chloride (1.34 g, 7.22 mmol) in 3 mL of THF was added. The cooling bath was removed and the reaction mixture was allowed to warm to room te perature. Stirring was continued at room temperature for 36 h. The solvent was removed in vacuo and the residue was dissolved in 125 mL of CH2Cl2. The mixture was washed with 40-mL portions of 10% aqueous NaHCO3, water and brine. The organic layer was dried over MgSO4 and concentrated. The residue was dissolved in 50 mL of ether and filtered through a short plug of silica gel. Concentration produced a light yellow solid which was dissolved in 30 mL of boiling petroleum ether (bp 37°–55° C.). The product precipitated upon standing at room temperature overnight. After cooling to 0° C. for several hours, the product was filtered and washed with a minimum of petroleum ether to produce 1.97 g (60% yield) of (1R,4S,5R)-8-phenylmenthyl-(S)-2-(4-phenylbenzoyloxy)-2-(6'-chloro-2'-methoxy-3'-methoxymethyl-4'-pyridyl)butyrate as a white solid (mp 100°–103° C.). $^1$H NMR: (300 MHz, CDCl3) δ 8.22 (d, 2 H, J =7 Hz), 7.05–7.80 (m, 13 H), 4.85 (m, 1 H), 4.50 (s, 2 H) 3.97 (s, 3 H), 3.16 (s, 3 H), 2.61 (m, 1 H) 0.55–2.35 (m, 21 H); $^1$H NMR: (1R,4S,5R)-8-phenylmenthyl (R)-2-(4-phenylbenzoyloxy)-2-(6'-chloro-2'-methoxy-3'-methoxymethyl-4'-pyridyl)butyrate (minor diastereomer): (300 MHz, CDCl3), δ 8.22 (d, 2 H, J=7 Hz) 7.05–7.80 (m, 13 H), 4.85 (m, 1 H), 4.62 (d, 1 H, J=9 Hz), 4.35 (d, 1 H, J=9 Hz), 3.90 (s, 3 H), 2.98 (s, 3 H), 2.62 (m, 1 H), 0.6–2.10 (m, 21 H).

EXAMPLE 15

Synthesis of (S)-2-hydroxy-2-(6'chloro-2'-methoxy-3'methoxymethyl-4'pyridyl)butyric acid by Saponification of (1R,4S,5R)-8-ohenvlmenthyl (S)-2-(4-phenylbenzoyloxy)-2-(6'-chloro-2'-methoxy-3'-methoxymethyl-4'-pvridyl)butyrate A solution of (1R,4S,5R)-8-phenylmenthyl-(S)-2-(4-phenylbenzoyloxy)-2-(6'-chloro-2'-methoxy-3'-methoxymethyl-4'-pyridyl)butyrate (201 mg, 0.294 mmol) in 6 mL of a 1:1 ethanol/2N NaOH was heated at 85°–90° C. for 12 h. Most of the ethanol was removed under reduced pressure and the residue was diluted with water (3 mL) and extracted with ether (3×4-mL). It is noteworthy that the chiral auxiliary ((−)8-phenylmenthol) was recovered in quantitative yield after evaporation of the ether extracts. The aqueous layer was acidified to a pH of 1 with 20% HCl and extracted with CH2Cl2 (3×5-mL). The combined organic layers were washed with water (2×5-mL) and brine (5 mL) and were dried over anhydrous Na2SO4. Concentration produced 142 mg of crude product which upon $^1$H NMR analysis was determined to be a 1:1 mixture of (S)-2-hydroxy-2-(6'chloro-2'-methoxy-3'methoxymethyl-4'pyridyl)-butyric acid and 4-biphenylcarboxylic acid. To this crude product was added 20 mL of hexanes, and, after bringing the solution to a boil, ethyl acetate was added dropwise until a clear homogeneous solution resulted. After standing at 25° overnight, the mixture was filtered, the solids were discarded, and the filtrate was concentrated to afford a colorless semi-solid. This process was repeated using 5 mL of hexanes and 2–3 drops of ethyl acetate to remove additional 4-biphenylcarboxylic acid. After concentration of the filtrate, 45 mg of (S)-2-hydroxy-2-(6'chloro-2'-methoxy-3'methoxymethyl-4'-pyridyl)butyric acid (76% yield) was obtained as a colorless viscous oil. $^1$H NMR 300 MHz (CDCl3) δ 7.13 (s, 1 H), 4.81 (d, 1 H, J=13 Hz), 4.55 (d, 1 H, J=13 Hz), 3.96 (s, 3 H), 3.39 (s, 3 H), 2.19 (m, 2 H), 1.01 (t, 3 H, J=7 Hz). This material was usable in subsequent synthetic steps requiring an optically pure compound without further purification.

The foregoing examples are illustrative of the present invention, and are not to be construed as limiting thereof. The invention is defined by the following claims, with equivalents of the claims to be included therein.

That which is claimed is:

1. A compound of the formula

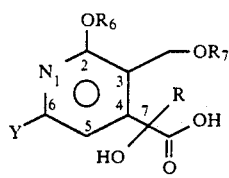
(XV)

wherein $R_6$ is lower alkyl, $R_7$ is lower alkyl, R is lower alkyl, and Y is H, F or Cl.

2. A compound according to claim 1, wherein $R_6$ is methyl or ethyl.

3. A compound according to claim 1, wherein $R_7$ is methyl or ethyl.

4. A compound according to claim 1, wherein R is ethyl.

5. A compound according to claim 1, wherein Y is H.

6. A compound according to claim 1, wherein Y is F or Cl.

7. A compound according to claim 1, wherein Y is Cl.

8. A compound of the formula

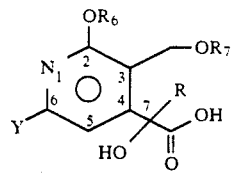
(XV)

wherein $R_6$ is lower alkyl, $R_7$ is lower alkyl, R is lower alkyl, and Y is H, F or Cl; and wherein said compound has the stereochemical orientation of Formula (XVa).

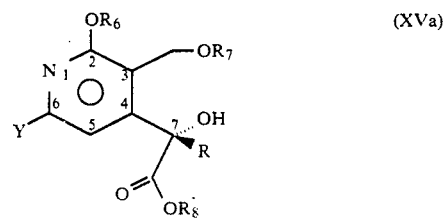
(XVa)

9. A compound according to claim 8, wherein said compound is optically pure.

10. A compound according to claim 8, wherein $R_6$ is methyl or ethyl.

11. A compound according to claim 8, wherein $R_7$ is methyl or ethyl.

12. A compound according to claim 8, wherein R is ethyl.

13. A compound according to claim 8, wherein Y is H.

14. A compound according to claim 8, wherein Y is F or Cl.

15. A compound according to claim 8, wherein Y is Cl.

* * * * *

UNITED STATES PATENT AND TRADEMARK OFFICE
CERTIFICATE OF CORRECTION

PATENT NO.   :   5,264,579
DATED        :   23 November 1993
INVENTOR(S)  :   Daniel L. Comins and Matthew F. Baevsky It is certified that error appears in the above-identified patent and that said Letters Patent is hereby corrected as shown below:

On title page, item [54] and col. 1, line 2, "CAMPTOTEHECIN" should read --CAMPTOTHECIN--.

Column 17, Line 64, correct "HCL" to read --HCl--.

Column 19, Line 58, correct "te perature." to read --temperature--.

Column 20, Line 23, correct "ohenvlmenthyl" to read --phenylmenthyl--.

Column 20, Line 25, correct "pvridyl)" to read --pyridyl--.

Signed and Sealed this

Third Day of May, 1994

Attest:

BRUCE LEHMAN

Attesting Officer

Commissioner of Patents and Trademarks